(12) United States Patent
Vija et al.

(10) Patent No.: US 8,090,429 B2
(45) Date of Patent: Jan. 3, 2012

(54) SYSTEMS AND METHODS FOR LOCALIZED IMAGE REGISTRATION AND FUSION

(75) Inventors: A. Hans Vija, Evanston, IL (US); Trudy Dayle Rempel, Glen Ellyn, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1494 days.

(21) Appl. No.: 10/881,638

(22) Filed: Jun. 30, 2004

(65) Prior Publication Data
US 2006/0004275 A1   Jan. 5, 2006

(51) Int. Cl.
*A61B 5/05* (2006.01)

(52) U.S. Cl. ........ 600/427; 600/425; 600/436; 382/282; 382/294

(58) Field of Classification Search .......... 600/436, 600/437, 440, 425–427; 382/282, 294
See application file for complete search history.

(56) References Cited

U.S. PATENT DOCUMENTS

| | | | |
|---|---|---|---|
| 5,672,877 A * | 9/1997 | Liebig et al. | 250/363.04 |
| 6,560,354 B1 * | 5/2003 | Maurer et al. | 382/131 |
| 6,728,424 B1 * | 4/2004 | Zhu et al. | 382/294 |
| 6,775,405 B1 * | 8/2004 | Zhu | 382/154 |
| 6,856,666 B2 * | 2/2005 | Lonn et al. | 378/8 |
| 6,950,494 B2 * | 9/2005 | Vija et al. | 378/62 |
| 2003/0128801 A1 * | 7/2003 | Eisenberg et al. | 378/19 |
| 2003/0146913 A1 * | 8/2003 | Shen et al. | 345/419 |
| 2003/0194050 A1 * | 10/2003 | Eberhard et al. | 378/37 |
| 2003/0216631 A1 * | 11/2003 | Bloch et al. | 600/407 |
| 2004/0066909 A1 * | 4/2004 | Lonn et al. | 378/901 |
| 2005/0013778 A1 * | 1/2005 | Green et al. | 424/9.6 |
| 2005/0015004 A1 * | 1/2005 | Hertel et al. | 600/425 |
| 2005/0031176 A1 * | 2/2005 | Hertel et al. | 382/128 |
| 2005/0065421 A1 * | 3/2005 | Burckhardt | 600/407 |
| 2008/0064949 A1 * | 3/2008 | Hertel et al. | 600/407 |

OTHER PUBLICATIONS

J.B. Antoine Maintz and Max A. Viergever, A Survey of Medical Image Registration, Image Sciences Institute, Utrecht University Hospital, Utrecht, the Netherlands (1997).

* cited by examiner

*Primary Examiner* — Brian Casler
*Assistant Examiner* — Christopher Cook
(74) *Attorney, Agent, or Firm* — Peter L. Kendall

(57) ABSTRACT

Systems and methods are described for co-registering, displaying and quantifying images from numerous different medical modalities, such as CT, MRI and SPECT. In this novel approach co-registration and image fusion is based on multiple user-defined Regions-of-Interest (ROI), which may be subsets of entire image volumes, from multiple modalities, where the each ROI may depict data from different image modalities. The user-selected ROI of a first image modality may be superposed over or blended with the corresponding ROI of a second image modality, and the entire second image may be displayed with either the superposed or blended ROI.

33 Claims, 2 Drawing Sheets

SYSTEMS AND METHODS FOR LOCALIZED IMAGE REGISTRATION AND FUSION

BACKGROUND OF THE INVENTION

1. Field of the Invention

The present invention is generally directed to medical imaging. More particularly, the present invention is directed to advanced image fusion systems and methods for use in image-assisted biopsy, image-assisted treatment planning, image-assisted treatment and image-assisted surgery, and molecular imaging.

2. Description of the Related Art

Nuclear medicine imaging tools, such as single-photon-emission-computed-tomography (SPECT) and positron-emission-tomography (PET) are known. Other types of medical imaging tools, such as magnetic resonance imaging (MRI), computed tomography (CT) or ultrasound (US), are also well known. Each of these known imaging techniques (modalities) provides a clinician with a different type of data and is useful for a different purpose, such as mainly functional (SPECT, PET) or mainly anatomical imaging (MR, CT, US). Until recently, images from only two modalities were combined in one display image. Combining these images usually requires two processes: 1) co-registration and 2) Image Fusion.

A medical imaging procedure typically creates a volume or matrix of measured values that forms the basis for that modality's image of the patient. Each value in the matrix represents image data at the geometric center of a voxel (volume element) of the volume. Co-registration is a process where the voxels in each of the images obtained by different modalities are transformed to correspond to a common reference frame. This can be done either via a rigid body or non-rigid body ("elastic") transformation of the pixel positions. In a rigid body transformation, only scaling, translations, and rotations are allowed, keeping the relative positions between all voxels constant. In an elastic transformation, additional to the fore-mentioned rigid body transformation, the voxel positions may also be elastically deformed, and relative distance between all voxels in the input image positions does not have to be preserved.

Image Fusion (IF) is a technique to display co-registered images obtained from two different imaging devices. IF can be characterized by the following: Let $I_i$ denote an image volume of modality $M_i$. In a previous step, separate image volumes from different devices are co-registered, in order to have image values at common pixel positions $\vec{r}_j = r_j^1 = r_j^2, \forall j$, with pixel index j within the coregistered volume. In the IF technique, the fused image $I_3$ of images $I_1$ and $I_2$ is displayed on a display device with the display-pixel color and intensity determined from a function of the coregistered image values of $I_1$ and $I_2$. The function is often, but not limited to a linear combination of the image pixel value in each image ("alpha-blending"), which can be easily mathematically represented by:

$$I_i = I_i(\vec{r}_j) \forall j;$$

$$I_3 = c_1 I_1 + c_2 I_2; \qquad \text{(Eq. 1)}$$

In general: $I_3 = f(I_1, I_2)$, where f may be any function combining the 2 images, however all pixels are involved.

By this technique, the images from two different devices or modalities (1 and 2) are displayed simultaneously in the same region in space, if the volumes are accurately co-registered. With current techniques, the entire image volumes of two images are fused using constant coefficients $c_1$ and $c_2$. The color table lookup index, T, is derived from $I_3$.

Current techniques are known to work well if images with similar resolution and noise characteristics are fused, or if the image information is equally distributed throughout the image volume in all images to be fused. However, if the resolution and noise characteristics are quite different, as is the case, for example, with functional and anatomical imaging, such as SPECT and CT images or MRI images, then the information delivered to an observer can be less than optimal, and more difficult to interpret with a simple IF technique. For example, referring to FIG. 1, the SPECT image of a prostate is fused with a CT image of the same prostate by the current IF technique. One can see that the critical information for the prostate in the center of the resulting image 100 is hard to read, because the entire SPECT image with its high noise and low spatial resolution is superimposed over the low-noise and high-spatial resolution CT image. In this example, the information of interest in the SPECT image is a small region of local uptake ("Region of Interest") corresponding to the functioning of the prostate, while the anatomical relevant information in the CT image is generally distributed throughout the entire image slice.

Current methods for combining images also fail to address the need of multi-modality imaging for quantitative use, treatment planning and monitoring, for systems with which more than two modality volumes could be registered, such as Ultrasound or CT, and SPECT/PET.

Another method to display co-registered images, shown in FIG. 3, provides two images from different devices or different modalities side by side. Here, areas of the images can be correlated by manipulating a correlated cursor 302, which points to the same region on each view. This method is also not optimal because the images are not overlaid at all, and the clinician is forced to make assumptions and estimations by visually comparing two separate images, with only the correlated cursor as an aid.

Accordingly, there is a need for new and improved systems and methods of combining image volumes from disparate imaging devices, to enhance clinical results and/or image-assisted biopsy, image-assisted treatment planning, image-assisted treatment and image-assisted surgery, and molecular imaging.

SUMMARY OF THE INVENTION

The present invention provides new and improved systems and methods for co-registering, displaying and quantifying images from different medical devices or imaging modalities. By blending or replacing planar Regions-of-Interest (ROI) and/or Volumes-of-Interest (VOI) from different imaging devices, a novel display with improved utility can be generated. The size and location of the ROI or VOI is determined by the type of imaging modality and the clinical user. Any number of different modalities may be combined into a single image such that the clinician can obtain the most useful image data in a single unified image. By registering and fusing selected ROIs and/or VOIs, rather than entire image volumes, processing may be reduced and real-time or near real-time images may be obtained.

In one embodiment of this novel approach, co-registration and image fusion are based on multiple (i.e., at least two) user-defined ROIs or VOIs. These ROIs or VOIs would be smaller than the entire coregistered volume, but larger than just a few pixels. The ROIs/VOIs of the object data would be coregistered with the information in the target data. This embodiment would be faster than classical coregistration or more accurate than Landmark registration. Classical co-registration is done by using information from the largest possible VOIs from each volume. Each voxel of one image modality is correlated to a corresponding voxel in another image modality, and using all possible voxels. Landmark co-registration is another well-known method, where the landmarks are the smallest possible ROIs, namely individual voxels. In Landmark co-registration, a user correlates a few points on each image modality that the user deems to relate to the same structure, and the whole image volume then can be co-registered by applying the transformation matrix that is derived from the selected landmark points. Beneficiaries are multi-modality fusion applications of diagnostic imaging, treatment planning, and monitoring.

In accordance with one embodiment of the present invention, a system for localized image fusion is provided. The system includes an image fusion unit configured to receive first and second imaging data respectively from first and second imaging devices. The unit is capable of registering the first imaging data with the second imaging data and blending a first region-of-interest (being a subset of the first imaging data) with a second region-of-interest (being a subset of the second imaging data). The first and second regions-of-interest correspond (e.g., relate to the same body part, etc.). The system may display a fused image comprising the first or second imaging data and the blended first and second regions-of-interest.

Further applications and advantages of various embodiments of the present invention are discussed below with reference to the drawing figures.

DETAILED DESCRIPTION OF THE PREFERRED EMBODIMENTS

Throughout this document, a Region-of-Interest (ROI) is meant to refer to a contractible, and thus a simply connected subset of image pixels within one slice (i.e. a two-dimensional plane) of a total image volume. The smallest ROI is one pixel, and the largest is the entire slice. A Volume-of-Interest (VOI) extends the notion of a ROI to three dimensions, with the smallest unit being a voxel, i.e. a three-dimensional pixel. That is, a VOI is a contractible, and thus simply connected subset of image voxels from the entire image volume in three dimensional space.

The present invention is able to produce blended images from disparate imaging devices, which produce data in different modalities. One advantage of the present invention is the ability to register and/or fuse a portion of a first image volume with a second image volume, without registering and/or fusing the entire image volumes. This is accomplished by allowing ROIs or VOIs to be selected (manually or automatically) for fusion. The selected ROIs or VOIs in one modality can be overlaid (i.e., superimposed) or blended with data from a corresponding ROI or VOI in a second modality.

Figure 1:
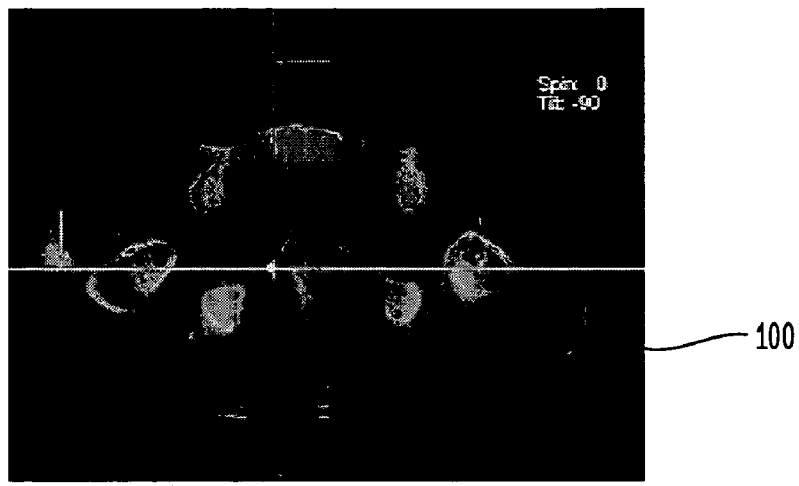
FIG. 1 is an image of a prior art fused image.
Figure 2:
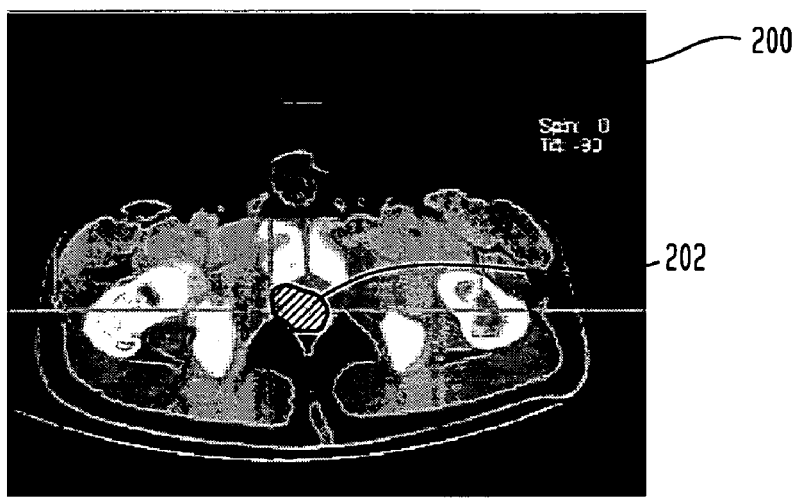
FIG. 2 is an image based in one modality with a region-of-interest displayed as a co-registration or blend of the first modality with image data of a second modality, according to an embodiment of the present invention.
Figure 3:
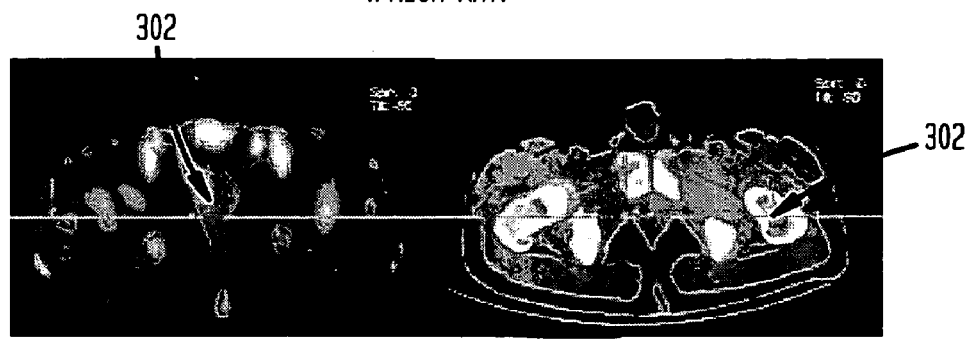
FIG. 3 is a prior art side-by-side image.

FIG. 2 shows an exemplary image created by the ROI fusion technique of the present invention. The region of interest in the functional SPECT object image is limited to the area of local uptake within a specific organ. The relevant information in the anatomical CT target image is distributed throughout the entire image slice. Within a coregistered CT image 200 (composed of multiple slices), an ROI 202 of a single slice of the image 200 corresponding to that specific organ is identified and selected for fusion. As shown, ROI 202 in the CT image is overlaid with the corresponding data from the same ROI in a nuclear SPECT image. That is, the entire image slice of CT image 200 remains intact except for the ROI 202. Thus, through the present invention, a clinician is capable of viewing any desired object image data from any one modality superposed on a target image from another modality, and yet is able to maintain the spatially accurate anatomical image from the second modality as a reference.

For simplicity, FIG. 2 shows the case of two modalities being blended in a single ROI, but the invention is not so limited and can be extended to more than two modalities and any number of ROIs and/or VOIs. For example, a CT image could have one ROI superimposed with ultrasound image data and a second ROI superimposed with nuclear medical image data.

Figure 4:
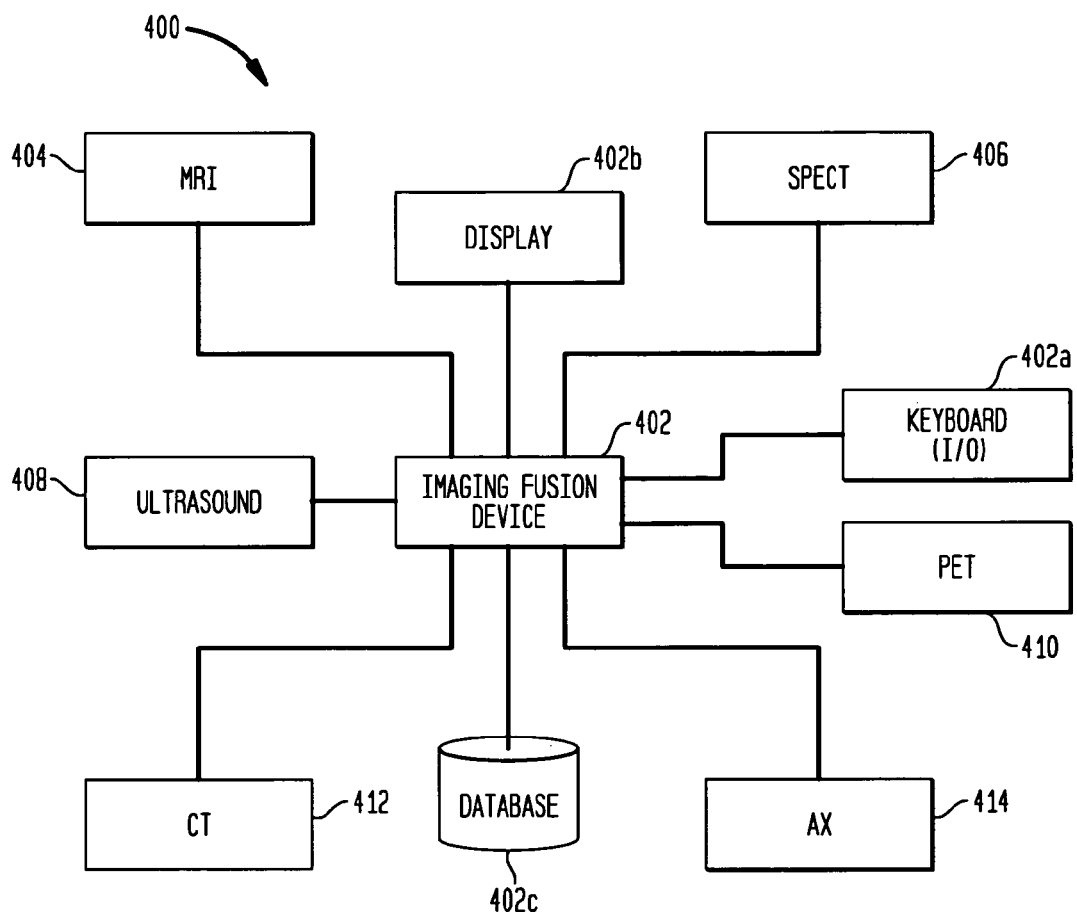
FIG. 4 is a block diagram of an imaging system according to an embodiment of the present invention.

FIG. 4 is a block diagram a system for image fusion of disparate imaging data according to an embodiment of the present invention. System 400 includes an image fusion device 402 coupled with two or more disparate imaging devices (i.e., different modalities), such as MRI unit 404, SPECT unit 406, Ultrasound unit 408, PET unit 410, CT unit 412 and AX (angioplasty X-ray) unit 414. Image fusion device 402 is configured to receive imaging data from each of the disparate imaging devices. Imaging data may be received in a common data protocol, such as the DICOM (Digital Imaging and COmmunication in Medicine) standard.

Image fusion device 402 is configured to process and filter image data as well as to co-register image voxel data received. Image fusion device 402 may include a client interface (not shown) to allow a user of the system to select ROIs and VOIs, display parameters, etc. according to the present invention. Accordingly, image fusion device 402 may include a keyboard or other I/O device 402a, a color video display monitor or other display device 402b, and memory (e.g., a database) 402c for storing image data, for example.

Image fusion device 402 may be any combination of hardware and software configured to perform the functions of the present invention, and may be in any configuration (central computer, distributed architecture, processing unit, etc.). In one exemplary embodiment, the system will include a graphical user interface (not shown) which allows a user of the system to view image data, select ROI and VOIs, view blended images, and other functionality described herein.

To create a combined or fused image, such as the image of FIG. 2, image data of two separate modalities (M1 and M2) are co-registered (i.e., their pixel (voxel) data is aligned). In this case, the CT data of the prostate is registered with the SPECT data of the same prostate. The entire image volumes need not be co-registered, but instead, selected ROI(s) or VOI(s) can be co-registered. Depending upon the type of registration performed, it may be more desirable to register only ROIs or only VOIs that are subsets of the entire image volume. For example, in a system using rigid body registration, when an ROI is of an organ that may move during the imaging period, such as the heart, then there is an advantage to registering the ROIs of the heart rather than the entire image.

Once the image data is co-registered, a composite image then can be constructed for the scaled ROI 202 of object data M1 displayed with color table T1, fused with full frame target data M2 displayed with color table T2. Through coregistration, the pixel locations of the ROI of the object M1 are registered and scaled to match the corresponding pixel locations and size of the target M2. Then, the coregistered ROI data of the first image M1 can be superposed with the corresponding ROI of the entire second target image M2. The color tables T1 and T2 can be set and scaled independently. The same alternatives could be used to display the entire first image M1 with a superposition of ROI data from second image M2. Techniques for co-registering image data are known. For example, many registration techniques are described in Maintz, J. B. A., & Viergever, M. A., *A Survey of Medical Image Registration, Navigated Brain Surgery* (1999), the entire contents of which are incorporated by reference herein.

The ROIs of the two images, M1 and M2, can be blended, and the blended ROI data superposed with the ROI of the partial or entire second image M2. A color table T3 of the ROI in M2 may be set independently from the full frame M2 image, so that the overlying M1 ROI data may appear semi-transparent or opaque, as controlled by the user (e.g., via a client interface).

The source images for M1 and M2 may be independently filtered with similar or different filters prior to display in the composite image.

Each ROI also is capable of showing time-stamped images and allowing for "movement" or flow depiction. For example, a CT image may be combined with an ultrasound image showing blood flow in an organ. The blood flow could be shown in blended ROI on the CT image. Therefore, when an ROI in an image is superimposed with image data from another device, the image data may be streaming in real-time or near real-time.

Image data can be mathematically represented by the following equation:

$$I_i = I_i(\vec{r}_j) \forall j \in \{ROI_{n-1}, \ldots, ROI_{n-N}\},$$

which may be mathematically summarized as $$I = \sum_{K}^{M} c_{nk} I_k; \quad \forall j \in \{ROI_{n=1}, \ldots, ROI_{n=N}\},$$

in general $I = f(I_1, \ldots, I_k)$, where f is any function, but where each image $I_n$, contains one or more $ROI_n$, and only the pixels within these ROI are used for the registration, and fusion or in general, and where M modalities are fused, with N ROIs having coefficients $c_{nk}$ (e.g., weights).

Interactive 3D-move/shape deformation and multi-modality may be displayed in object data ROI. The ROI/VOI may be generated on single modality displays of either image or on the composite image.

The ROI/VOI also may be generated by a combination (i.e. union or intersection) of ROIs/VOIs and/or of separate ROI/VOIs created in either image, or on the composite image. The ROI/VOI may be created, moved or resized by user operations on single modality displays of either image, or on the composite image. The ROI may be a projection of a 3D VOI.

3D ROI embedded maximum intensity projection (MIP) may be generated and displayed (i.e., MIP of M1 over MIP of M2). Through coregistration, the pixel locations of the VOI of M1 are registered and scaled to match the pixel locations and size of M2. A first MIP image is made up of the selected VOI of the object M1. The scaled VOI of M1 replaces the same registered VOI of the target M2. A MIP image of the combined volume is then created. The scaling intensity and color table type of T1 and T2 that are used to create the display pixel appearance of the combined projection can be adjusted independently by the user.

A second or alternate MIP image is then made up of intensity-scaled VOI of M2. The object VOI of M2 is added to the same registered VOI of the target M1. The scaling intensity and color table type of T1 and T2 that are used to create the display pixel appearance of the combined projection can be adjusted independently by the user.

A third or combined MIP image is then made up of intensity-scaled VOI of M1 and M2. Through coregistration, the VOI of M1 is registered and scaled to match the pixel location and size of the target M2. The scaled VOI of M1 is added to a scaled version of the same registered VOI of M2. The combined VOI replaces the same registered VOI of the target M2. A MIP image of the combined volume is then created. The scaling intensity and color table type of the VOI in M1 and the VO1 in M2 that are used to create the combined VOI can be adjusted independently by the user.

Images from modalities M1 and M2 may be segmented into separate organ or shape zones by a segmentation technique. The image correlation and coherence between the co-registered images is reported by zone and segmentation technique.

The present invention can be extended to more than two modalities, where all but one of the modalities represent the object modalities and the remaining one modality represents the target modality, i.e. different ROIs may show various modality information.

The present invention can be extended to multiple image series in two or more modalities, where all of the series in one modality and all but one of the series in the second modality represent the object modality, and the remaining one image in the second modality represents the target modality. In this explanation, series may mean images acquired at different times, in different studies, dynamic images, gated images, or other combinations. Each of the images may be independently registered with the target image.

The present invention can be used for manual and semi-automatic registration, or to either initialize or fine tune auto-registration, where structures within ROIs are used for registration.

One skilled in the art will understand that the present invention can be extended and used for interventional procedures, as well as for Partial Volume Correction.

Thus, a number of preferred embodiments have been fully described above with reference to the drawing figures. Although the invention has been described based upon these preferred embodiments, it would be apparent to those of skilled in the art that certain modifications, variations, and alternative constructions would be apparent, while remaining within the spirit and scope of the invention.

What is claimed is:

1. A system for localized image fusion, comprising:
an image fusion unit configured to receive target and object imaging data respectively from first and second disparate imaging devices, to register a selected region of interest within said target imaging data with a corresponding region of interest of said object imaging data, wherein said selected region of interest is a subset of said target imaging data, to blend imaging data of said registered regions of interest to provide a first blended image of said selected region of interest, and to display a composite image comprising said entire target imaging data fused with said first blended image.

2. The system as recited in claim 1, wherein said target imaging data is anatomical (e.g. CT) data and said object imaging data is functional (e.g. SPECT) data.

3. The system as recited in claim 1, wherein said image fusion unit is further configured to receive third imaging data from a third imaging device of a modality different from said first and second imaging devices, to register a selected region of interest within said target imaging data with a corresponding region of interest of said third imaging data to obtain a registered third region of interest, to blend imaging data of said registered third region of interest to provide a second blended image of said registered third region of interest, and to display a composite image comprising said entire first imaging target data fused with the first and second blended images.

4. The system as recited in claim 3, wherein said first blended image is a weighted sum or combination of said target and object regions of interest, said object region of interest being given a weight higher or independently variable than a weight given said target region of interest, and said second blended image is a weighted sum or combination of said target and third imaging data regions of interest, said third imaging data region of interest being given a weight higher or independently variable than a weight given said object region of interest.

5. The system as recited in claim 1, wherein said first blended image is based on giving said object region of interest a display weight higher or independently variable than a weight given said target region of interest.

6. The system as recited in claim 1, wherein said first blended image is a weighted sum or combination of said target and object regions of interest, said object region of interest being given a weight higher or independently variable than a weight given said target region of interest.

7. The system as recited in claim 1, further comprising a color display monitor for displaying said first blended image.

8. The system as recited in claim 1, wherein said object imaging data is anatomical (e.g. CT) data and said target imaging data is functional (e.g. SPECT) data.

9. A method for image registration and fusion, comprising the steps of:
receiving first image data of a first modality;
receiving second image data of a second modality different from said first modality;
registering at least one portion of said first image data with a corresponding portion of said second image data;
blending image data of said registered portions to create a first blended image; and
rendering a composite image comprising said entire second image data fused with said first blended image.

10. The method according to claim 9, wherein said step of blending comprises a step of summing or combining pixel data of said at least one portion of said first image data with pixel data of said corresponding portion of said second image data to form said first blended image or the display information for the registered portions.

11. The method according to claim 9, wherein said rendering step includes a step of displaying said entire second image data with a first color format and said first blended image in a second color format, said first blended image being displayed in a location corresponding to said corresponding portion.

12. A system for localized image fusion, comprising:
an image fusion unit configured to receive first and second imaging data respectively from first and second imaging devices, to register said first imaging data with said second imaging data, to blend image data of a first region of interest within said first imaging data with image data of a corresponding region of interest within said second imaging data to obtain a blended image, and to display a composite image comprising said entire first imaging data fused with said blended image, and/or to display a composite image comprising said entire second imaging data fused with said blended image.

13. A system for localized image fusion, comprising:
an input means for receiving first and second imaging data respectively from first and second imaging devices;
a registration means for registering said first imaging data with said second imaging data
a blending means for blending image data of a first region of interest within said first imaging data with image data of a corresponding region of interest within said second imaging data to obtain a first blended image; and
a display means for displaying a composite image comprising said entire first imaging data fused with said first blended image.

14. The system as recited in claim 13, wherein said first imaging data is anatomical data and said second imaging data is functional data.

15. The system as recited in claim 13, wherein said input means receives third imaging data from a third imaging device, said blending means blends image data of a third region of interest within said first imaging data with image data of a corresponding region of interest within said third imaging data to obtain a second blended image, and said display means displays a composite image comprising said entire first imaging data fused with said first and second blended images.

16. The system as recited in claim 15, wherein said first blended image is a weighted sum of image data of said corresponding regions of interest of said first and second imaging devices, image data of said second imaging device being given a weight higher than a weight given image data of said first imaging device, and said second blended image is a weighted sum of image data of said corresponding regions of interest of said first and third imaging devices, image data of said third imaging device being given a weight higher than a weight given image data of said first imaging device.

17. The system as recited in claim 13, wherein said blending means weights the combination of image data of said corresponding regions of interest during said blending.

18. The system as recited in claim 17, wherein said first blended image is a weighted sum of image data of said corresponding regions of interest, image data of said second imaging device being given a weight higher than a weight given image data of said first imaging device.

19. The system as recited in claim 13, wherein said first imaging data is functional data and said second imaging data is anatomical data.

20. An image fusion system, comprising:
a plurality of imaging devices, at least two devices of said plurality generating image data of different modalities;
an image fusion unit coupled with said plurality of imaging devices and configured to receive first and second imaging data respectively from first and second imaging devices of said plurality of imaging devices, to register said first imaging data with said second imaging data, to blend image data of a region of interest within said first imaging data with image data of a corresponding region of interest within said second imaging data to obtain a first blended image, and to display a composite image comprising said entire first imaging data fused with said first blended image.

21. The system as recited in claim 20, wherein said first imaging device comprises a CT scanner and said second imaging device comprises a nuclear imaging device.

22. The system as recited in claim 20, wherein said image fusion unit is further configured to receive third imaging data from a third imaging device, to blend image data of a selected region of interest within said first imaging data with image data of a corresponding region of interest within said third imaging data to obtain a second blended image, and to display a composite image comprising said entire first imaging data fused with said first and second blended images.

23. The system as recited in claim 22, wherein said first blended image is a weighted sum of image data of said corresponding regions of interest of said first and second imaging devices, image data of said second imaging device being given a weight higher than a weight given image data of said first imaging device, and said second blended image is a weighted sum of image data of said corresponding regions of interest of said first and third imaging devices, image data of said third imaging device being given a weight higher than a weight given image data of said first imaging device.

24. The system as recited in claim 20, wherein said first blended image is based on giving said second image data a display weight higher or independently variable than a weight given said first image data.

25. The system as recited in claim 20, further comprising a color display monitor for displaying said blended image.

26. The system as recited in claim 20, wherein said first imaging device comprises an Ultrasound device and said second imaging device comprises a nuclear imaging device.

27. The system as recited in claim 20, wherein said first imaging device comprises a CT device and said second imaging device comprises a SPECT device.

28. An image fusion device, comprising:
an input unit for receiving imaging data from disparate imaging devices;
a graphic user interface configured to display said imaging data, to allow selection of regions-of-interest within said imaging data to be blended, and to display a composite image; and
a processing unit coupled with said input unit and said graphical user interface and configured to co-register said imaging data from disparate imaging devices, to blend image data of selected regions-of-interest within said imaging data from said imaging devices to obtain a blended image, and to generate display data for a composite image comprising the entirety of imaging data from one of said imaging devices fused with said blended image.

29. The system as recited in claim 28, wherein said imaging data includes first image data and second image data corresponding to first and second imaging devices respectively;
said interface is configured to allow selection of a first region-of-interest (ROI) within said first imaging data and a second region-of-interest (ROI) within said second imaging data;
said processing unit is configured to co-register said first imaging data with said second imaging data and to blend image data of said first ROI with image data of said second ROI to create a first blended image, and to generate display data comprising said entire first image data fused with said first blended image.

30. The system as recited in claim 29, wherein said first imaging data is CT data and said second imaging data is SPECT data.

31. The system as recited in claim 29, wherein said imaging data includes third imaging data from a third imaging device;
said interface is configured to allow selection of a third ROI from said third imaging data and to select a fourth ROI from said first imaging data;
said processing unit is configured to co-register said first imaging data with said third imaging data and to blend image data of said third ROI with image data of said fourth ROI to create a second blended image, and to generate display data comprising said entire first image data fused with said first and second blended images.

32. The system as recited in claim 31, wherein said first and second blended images are generated based upon giving image data of said second imaging device a weight higher than a weight given image data of said first imaging device and giving image data of said third imaging device a higher weight than image data of said first imaging device.

33. The system as recited in claim 28, wherein said system is configured to display an entire single image in a first modality having a plurality of ROIs superimposed with data from images of other modalities.

\* \* \* \* \*